(12) United States Patent
Stürzebecher et al.

(10) Patent No.: US 6,831,196 B2
(45) Date of Patent: Dec. 14, 2004

(54) UROKINASE INHIBITORS

(75) Inventors: Jörg Stürzebecher, Erfurt (DE);
Torsten Steinmetzer, Jena (DE);
Andrea Schweinitz, Jena (DE)

(73) Assignee: Curacyte AG, Munich (DE)

( * ) Notice: Subject to any disclaimer, the term of this patent is extended or adjusted under 35 U.S.C. 154(b) by 43 days.

(21) Appl. No.: 10/297,557

(22) PCT Filed: Jun. 15, 2001

(86) PCT No.: PCT/EP01/06789

§ 371 (c)(1),
(2), (4) Date: Dec. 9, 2002

(87) PCT Pub. No.: WO01/96286

PCT Pub. Date: Dec. 20, 2001

(65) Prior Publication Data

US 2003/0166576 A1 Sep. 4, 2003

(30) Foreign Application Priority Data

Jun. 15, 2000 (DE) ........................................ 100 29 014

(51) Int. Cl.[7] ........................ C07C 233/05; A61K 31/16

(52) U.S. Cl. ........................ 564/157; 564/92; 564/147; 560/29; 558/248; 514/485; 514/512; 514/604; 514/614; 514/617; 514/616

(58) Field of Search ........................ 558/248; 560/29; 564/92, 157, 147; 514/512, 485, 604, 617, 614, 616

(56) References Cited

FOREIGN PATENT DOCUMENTS

| EP | 0183271 A2 | | 6/1986 |
|---|---|---|---|
| WO | WO 94/29336 | | 12/1994 |
| WO | WO 95/17885 | | 7/1995 |
| WO | WO 99/05096 | | 2/1999 |
| WO | 0004954 | * | 2/2000 |
| WO | WO 00/05245 | | 2/2000 |

OTHER PUBLICATIONS

Baker et al., "Inhibition of Cancer Cell Urokinase Plasminogen Activator by its Specific Inhibitor PAI–2 and Subsequent Effects on Extracellular Matrix Degradation," *Cancer Research* 50:4676–4684 (1990).
Bookser et al., "Syntheses of Quadruply Two–and Three–Atom, Aza–Bridged, Cofacial Bis (5, 10, 15, 20–Tetraphenylporphyrins)," *J. Am. Chem. Soc.* 113:4208–4218 (1991).
Cajot et al., "Plasminogen–Activator Inhibitor Type 1 is a Potent Natural Inhibitor of Extracellular Matrix Degradation by Fibrosarcoma and Colon Carcinoma Cells," *Proc. Natl. Acad. Sci.* 87:6939–6943 (1990).
Duggan et al., "Urokinase Plasminogen Activator and Urokinase Plasminogen Activator Receptor in Breast Cancer," *Int. J. Cancer* 61:597–600 (1995).

Frerot et al., "PyBOP®[1] and PyBrop: Two Reagents for the difficult Coupling of the α, α–Dialkyl Amino Acid, Alb.," *Tetrahedron* 47:259–270 (1991).
Gustafsson et al., "Effects of Inogatran, A New Low–Molecular–Weight Thrombin Inhibitor, in Rat Models of Venous and Arterial Thrombosis, Thrombolysis and Bleeding Time," *Blood Coagulation and Fibrinolysis* 7:69–79 (1996).
Judkins et al., "A Versatile Synthesis of Amidines from Nitriles Via Amidoximes." *Synthetic Communications* 26:4351–4367 (1996).
Kettner et al., "Inactivation of Trypsin–Like Enzymes with Peptides of Arginine Chloromethyl Ketone," *Methods in Enzymology* 80:826–842 (1981).
Kunzel et al., "4–Amidinobenzylamine–Based inhibitors of Urokinase," *Bioorganic & Medicinal Chemistry* 12:645–648 (2002).
Mignatti et al., "Biology and Biochemistry of Proteinases in Tumor Invasion," *Physiological Reviews* 73:161–195 (1993).
Ossowski et al., "Antibodies to Plasminogen Activator Inhibit Human Tumor Metastasis," *Cell* 35:611–619 (1983).
Pedersen et al., "Prognostic Impact of Urokinase, Urokinase Receptor, and Type 1 Plasminogen Activator Inhibitor in Squamous and Large Cell Lung Cancer Tissue," *Cancer Research* 54:4671–4675 (1994).
Reuning et al., "Multifunctional Potential of the Plasminogen Activation System in Tumor Invasion and Mestatasis (Review)," *International Journal of Oncology* 13:893–906 (1998).
Schmitt et al., "Clinical Impact of the Plasminogen Activation System in Tumor Invasion and Metastasis: Prognostic Relevance and Target for Therapy," *Thrombosis and Haemostasis* 78:285–296 (1997).
Sperl et al., (4–Aminomethyl) Phenylguanidine Derivatives as Nonpeptidic Highly Selective Inhibitors of Human Urokinase, *Proc. Natl. Acad. Sci. USA* 97:5113–5118 (2000).
Stephens et al., "The Urokinase Plasminogen Activator System as a Target for Prognostic Studies in Breast Cancer," *Breast Cancer Research and Treatment* 52:99–111 (1998).
Sturzebecher et al., "3–Amidinophenylalanine–Based Inhibitors of Urokinase," *Bioorganic & Medicinal Chemistry Letters* 9:3147–3152 (1999).
Sturzebecher et al., "Synthetische Inhibitoren der Serinproteinasen," *Pharmazie* 33:599–602 (1978).

(List continued on next page.)

Primary Examiner—Shailendra Kumar
(74) Attorney, Agent, or Firm—Clark & Elbing LLP

(57) ABSTRACT

The invention relates to a highly active, highly specific urokinase inhibitor which is suitable for therapeutic applications and can be synthesized in an extremely simple manner. Surprisingly, it was found that amidino benzylamine derivatives, especially 4-amidino-benzylamine, with two bonded amino acids represent a new group of highly active and very selective uPA inhibitors. The urokinase inhibitors can be used in medical applications, e.g. in the treatment of malign tumors such as in cases of metastatic spread.

5 Claims, No Drawings

OTHER PUBLICATIONS

Tamura et al., "Synthesis and Biological Activity of Peptidly Aldehyde Urokinase Inhibitors," *Bioorganic & Medicinal Chemistry Letters* 10:983–987 (2000).

Towle et al., "Inhibition of Urokinase by 4–Substituted Benzo[b]thiopene–2–Carboxamindines: An Important New Class of Selective Synthetic Urokinase Inhibitor," *Cancer Research* 53:2553–2559 (1993).

Tucker et al., "Potent Noncovalent Thrombin Inhibitors that Utilize the Unique Amino Acid D–Dicyclohexylalanine in the P3 Position. Implications on Oral Bioavailability and Antithrombotic Efficacy," *J. Med. Chem.* 40:1565–1569 (1997).

Tucker et al., "Synthesis of a Series of Potent and Orally Bioavailable Thrombin Inhibitors that Utilize 3,3–Disubstituted Propioinic Acid Derivatives in the $P_3$ Position," *J. Med. Chem.* 40:3687–3693 (1997).

Vassalli et al., "Amiloride Selectively Inhibits the Urokinase–Type Plasminogen Activator," *FEB* 214:187–191 (1987).

Wagner et al., "Synthese von N–[Amidinobenzyl]–und N–[Amidinophenyl]–phthalimide und –1–Oxoisoindoline," *Pharmazie* 32:76–79 (1977).

* cited by examiner

UROKINASE INHIBITORS

This application is the U.S. National Stage of International Application No. PCT/EP01/06789, filed Jun. 15, 2001, which claims the benefit of German Application No. 10029014.0, filed Jun. 15, 2000.

DESCRIPTION

The invention relates to novel inhibitors of urokinase for treating malignant tumors and metastasis.

The dissemination and metastasis of solid tumors in surrounding tissue is made possible by their ability to break down the extracellular matrix in the environment of the tumor cell and/or penetrate the basal membrane. Aside from various matrix metalloproteinases and cathepsins, the plasminogen activator urokinase (uPA) is, in particular, of central importance in this process (P. Mignatti and D. B. Rifkin, Physiol. Rev. 73, 161–195, 1993). Thus, uPA activates plasminogens; the resulting plasmin is able to break down the components of the extracellular matrix (fibrin, fibronectin, laminin and proteoglycans inter alia) and also activate metalloproteases and prourokinase to give uPA (U. Reuning et al., Int. J. Oncol. 13, 893–906, 1998). Both prourokinase and uPA bind to the uPA receptor (uPAR), which is a specific receptor located on the cell surface. This results in the activity of uPA, and consequently plasminogen activation, being augmented and focused in the direct environment of the tumor cell. The importance of this cell-associated plasminogen activator system for tumor growth and tumor dissemination has been demonstrated both in cell-biological studies and in animal models. Thus, the invasive potential of tumor cells is diminished by inhibiting the enzymatic activity of uPA with the natural inhibitors PAI-1 and PAI-2 (J.-F. Cajot et al., Proc. Natl. Acad. Sci. USA 87, 6939–6943, 1990; M. Baker et al., Cancer Res. 50, 4876–4684, 1990). In chick embryos, the formation of lung metastases caused by human carcinoma cells was almost completely inhibited by adding antibodies directed against uPA (L. Ossowski et al., Cell 35, 611–619, 1983).

In recent years, the clinical relevance of the factors involved in the plasminogen activator system (uPA, uPAR, PAI-1 and PAI-2) for the prognosis of patients who have solid malignant tumors has been intensively investigated. In particular, the content of uPA in the tissue of various tumors has been found to be a prognosis factor. Thus, patients who have a high uPA level have a poorer prognosis than do those who have a low uPA concentration in the tumor (M. Schmitt et al., Thromb. Haemost. 78, 285–296, 1997; R. W. Stephens et al., Breast Cancer Res. Treat. 52, 99–111, 1998). An elevated concentrations of uPAR in the tumor tissue is also correlated with a poor prognosis (H. Pedersen et al., Cancer Res. 54, 4671–4675, 1994; C. Duggan et al., Int. J. Cancer 61, 597–600, 1995).

From the findings regarding the prognostic value of the uPA content and uPAR content in tumor tissue, it can be assumed that synthetic uPA inhibitors are able to suppress the invasion and dissemination of tumor cells. However, the number of uPA inhibitors which are known thus far is relatively small. The majority possess only slight specificity and potency, as is the case for various benzamidine and β-naphthamidine derivatives (J. Stürzebecher and F. Markwardt, Pharmazie 33, 59–602, 1978). While the amiloride which is described by Vassalli and Belin (FEBS Letters 214, 187–191, 1997) as being a uPA inhibitor is a specific inhibitor of uPA, the inhibition is only weak ($k_i$=7 μM).

4-Substituted benzothiophene-2-carboxamidines have been found to be more active uPA inhibitors ($K_i$=0.16 μM in the case of compound 623). Inhibitors of this type also inactivate uPA which is bound to uPAR (M. J. Towle et al., Cancer Res. 53, 2553–2559, 1993). The benzothiophene derivatives are very specific and they only have a low inhibitory effect on plasmin and tissue-type plasminogen activator (tPA); however, it is a very elaborate matter to synthesize compounds of this type.

While 4-aminomethylphenylguanidine derivatives have a comparable specificity, their inhibitory effect on uPA ($K_i$= 2.4 μM for the most active compound) is comparatively low (S. Sperl et al., Proc. Natl. Acad. Sci. USA 97, 5113–5118, 2000).

In contrast to this, Nα-triisopropylphenylsulfonyl-3-amidinophenylalanine derivatives achieve micromolar $K_i$ values (0.41 μM in the case of the most active compound); however, they are very nonspecific uPA inhibitors, having the same or a stronger inhibitory effect on trypsin, thrombin and plasmin (J. Stürzebecher et al., Bioorg. Med. Letters 9, 3147–3152, 1999). WO 99/05096 discloses improved β-naphth-amidines which are very effective uPA inhibitors. While this patent reports $IC_{50}$ values in the nanomolar range, it provides no data with regard to selectivity and biological activity.

Thus far, only a few peptides which are derived from the substrate sequence have been reported to be uPA inhibitors. Kettner and Shaw (Methods in Enzymology, 80, 826–842, 1981) described chloromethyl ketones which, while inhibiting uPA irreversibly, are not suitable for in-vivo use.

EP 18 32 71 discloses lysine derivatives which inhibit uPA to a certain degree; however, they also inhibit other comparable enzymes and can consequently only be used very specifically, or in a restricted manner, for medical purposes. The same applies to the low molecular weight polypeptides (approx. 50 amino acids) which are reported in WO 95/17885 to be uPA inhibitors and which are derived from natural inhibitors. Their peptide nature, and their molecular size, greatly restrict their in-vivo use.

However, WO 00/05245 has very recently reported peptidyl aldehydes which contain an argine C-terminally and a D-serine in P3 and which effectively inhibit uPA. However, the aldehyde function gives rise to instability and low selectivity. After the Ser hydroxyl had been acylated, the key compound iBuOCO-D-Ser-Ala-Arg-H was observed to have a relative bioavailability of 87% following s.c. administration (S. Y. Tamura et al., Bioorg. Med. Chem. Lett. 10, 983–987, 2000). Furthermore, notable advances, with regard to both the inhibitory effect and the bioavailability, were achieved when using tripeptide derivatives of the D-Phe-Pro-Arg type in the search for inhibitors of thrombin, an enzyme which is related to uPA, when agmatine, trans-4-aminomethylcyclohexylamine or 4-amidinobenzylamine was incorporated C-terminally. Picomolar $K_i$ values were achieved and the oral bioavailability was improved (T. J. Tucker et al., J. Med. Chem. 40, 1565–1569 and 3687–3693, 1997); however, no uPA inhibitors were found. Thus, while melagatran, which possesses a 4-amidinobenzylamide residue C-terminally, inhibits trypsin ($K_i$=2.0 nM) and thrombin ($K_i$=2.0 nM) very nonspecifically, its inhibition of uPA, with a $K_i$=6.3 μM, is three orders of size weaker (D. Gustafsson et al., Blood Coagul. Fibrinolysis 7, 69–79, 1996; WO 94/29336).

The invention is based on the object of specifying an active compound which inhibits urokinase with high activity and specificity, which can be prepared by means of a synthesis which is as uncomplicated as possible, and which is also suitable for therapeutic applications.

Surprisingly, it has been found that acylated amidinobenzylamine in accordance with the formula I cited in patent claim 1, in particular compounds of 4-amidinobenzylamine in which X, $R_1$, $R_2$ and $R_3$ give natural and/or unnatural amino acids, inhibit urokinase very effectively and selectively. In this connection, amidinobenzylamine forms a particularly active urokinase inhibitor if the amidino group is in the 4 position, Gly and D-Ser are bonded as amino acids and the compound possesses an N-terminal protecting group $R_4$ which is composed of an arylsulfonyl radical or aralkylsulfonyl radical.

Esters, in particular those with oxycarboxylic acids, can be employed as prodrugs if they are hydrolyzed during the course of enteral uptake. It has also been found, surprisingly, that some of these oxycarbonyl derivatives of the compounds according to the invention are also very strong urokinase inhibitors.

Aside from urokinase, the glycine derivatives inhibited other enzymes to a markedly lesser degree, which means that these amidinobenzylamine derivatives according to the invention constitute a novel group of highly active and very selective uPA inhibitors. By contrast, compounds which do not carry any H as $R_1$ (e.g. alanine derivatives) no longer inhibit urokinase selectively but are also strong inhibitors of trypsin, thrombin and plasmin.

As a rule, the compounds are present as salts with mineral acids, preferably as hydrochlorides, or as salts with suitable organic acids.

The compounds of the formula I can be prepared in a relatively simple manner using known methods, as described below:

The starting compound 4-cyanobenzylamine is prepared by Gabriel synthesis (G. Wagner and I. Wunderlich, Pharmazie 32, 76–77, 1977; B. C. Bookser and T. C. Bruice, J. Am. Chem. Soc. 113. 4208–4218, 1991) from 4-cyanobenzyl bromide. The Boc-protected acetyloxamidinobenzylamine is obtained from the 4-cyanobenzylamine which has been prepared in this way. The other amino acids and the $R_4$ protecting group are coupled on employing standard coupling methods and using Boc as the N-terminal protecting group. The second amino acid can also be coupled directly as an N-arylsulfonyl- or N-aralkylsulfonyl-protected amino acid. The peptide analogs are synthesized sequentially, beginning with the acetyloxamidinobenzylamine. In order to synthesize the corresponding esters, the target compound is reacted with the corresponding acid chloride. Most of the products crystallize well and can be readily purified in this way. In the final step, the inhibitors are purified by means of preparative, reversed-phase HPLC.

The invention will be explained in more detail below with the aid of two implementation examples:

IMPLEMENTATION EXAMPLE 1

Synthesizing benzylsulfonyl-D-Ser-Gly-4-amidinobenzylamide×HCl 1.1 Boc-4-cyanobenzylamide 20 g (0.151 mol) of 4-cyanobenzylamine were dissolved in 300 ml of $H_2O$, 150 ml of dioxane and 150 ml of 1 N NaOH. While cooling with ice, 37.5 ml of di-tert-butyl dicarbonate were added dropwise and the mixture was stirred at 0° C. for one hour and at room temperature for a further 24 hrs. The dioxane was removed in vacuo and the aqueous residue was extracted 3 times with ethyl acetate. The combined extracts were washed 3 times with a 5% solution of $KHSO_4$ and 3 times with a saturated solution of NaCl, dried over $Na_2SO_4$ and concentrated in vacuo (white crystals). HPLC: acetonitrile/$H_2O$, elution at 44.1% acetonitrile; yield: 30.48 g (0.131 mol), 87%.

1.2 Boc-4-acetyloxamidinobenzylamide

As described by Judkins et al. (Synthetic Comm. 26, 4351–4367, 1996), 30.48 g (0.131 mol) of Boc-4-cyanobenzylamide were dissolved in 300 ml of abs. ethanol together with 13.65 g (0.197 mol) of hydroxylamine×HCl and 34 ml (0.197 mol) of DIEA. The mixture was boiled under reflux for 2 hrs and stirred overnight at room temperature. After that, the mixture was concentrated in vacuo and the residue was dissolved in approx. 200 ml of acetic acid and treated with 18.67 ml (0.197 mol) of acetic anhydride. After 1 hr, the mixture was concentrated once again and the residue was dissolved in ethyl acetate and this solution was washed in each case 3 times, at 0° C., with a 5% solution of $KHSO_4$ and a saturated solution of NaCl. After drying over $Na_2SO_4$ and concentrating in vacuo, a white powder was obtained. HPLC: acetonitrile/$H_2O$, elution at 32.0% acetonitrile; yield: 31.3 g (0.102 mol) 78%.

1.3 4-Acetyloxamidinobenzylamine×HCl 5 mmol of Boc-4-acetyloxamidinobenzylamide are dissolved in 20 ml of 1 N HCl in glacial acetic acid and the solution is left to stand at room temperature for 45 min. The mixture is then extensively concentrated in vacuo, after which the product is precipitated with dry diethyl ether, sintered off, washed once again with fresh ether, and dried in vacuo. In view of the quantitative conversion, the product was used for the next synthesis step without being purified any further.

1.4 Boc-Gly-4-acetyloxamidinobenzylamide

Boc-Gly-OH (Orpegen, Heidelberg) was coupled to 4-acetyloxamidinobenzylamine in accordance with Frérot et al. (Tetrahedron 47, 259 ff., 1991). For this, 2.064 g (9.3 mmol) of 4-acetyloxamidinobenzylamine×HCl and 1.629 g (9.3 mmol) of Boc-Gly-OH were dissolved in approx. 25 ml of DMF. 4.84 g (9.3 mmol) of PyBOP and 3.878 ml (27.9 mmol) of TEA were then added at 0° C. and the pH was adjusted to 9 with TEA. After the mixture had been stirred at room temperature for 1 hr, it was concentrated in vacuo and the residue was taken up in ethyl acetate and this solution was washed, in each case 3 times, acidically, basically and neutrally, after which it was dried and concentrated. Yield: 3 g (8.2 mmol) 88%.

1.5 Boc-Gly-4-amidinobenzylamide×AcOH 3 g (8.2 mmol) of Boc-Gly-4-acetyloxamidinobenzylamide were dissolved in 200 ml of 90% acetic acid. 300 mg of 10% palladium on active charcoal were then added under argon. The argon was replaced with a hydrogen atmosphere and the mixture was hydrogenated for 24 hrs while being stirred vigorously. The catalyst was filtered off and the filtrate was concentrated in vacuo. Yield: 2.9 g (7.9 mmol) 96%.

1.6 H-Gly-4-amidinobenzylamide×2 HCl 2.9 g (7.9 mmol) of Boc-Gly-4-amidinobenzylamide were dissolved in 100 ml of 1 N HCl in glacial acetic and the solution was left to stand at room temperature for 45 min. It was then extensively concentrated in vacuo and the residue was precipitated with dry diethyl ether; after that, it was sintered off and the product was washed once again with fresh ether. After the product had been dried in vacuo, it was used without any further purification for the synthesis as described in item 1.8.

1.7 Benzylsulfonyl-D-Ser(Bz)-OH 229 mg (1.173 mmol) of H-D-Ser(Bz)-OH (Bachem, Heidelberg) and 408 µl (2.345 mmol) of DIEA were dissolved in 50 ml of 50% acetonitrile. 335 mg (1.76 mmol) of benzylsulfonyl chloride were then added and the mixture was stirred at room temperature for 12 hrs. It was then concentrated in vacuo and the residue was taken up with ethyl acetate and this mixture was washed, in each case 3 times, acidically and neutrally. After drying over sodium sulfate, the mixture was concentrated in vacuo. Yield: 289 mg (0.827 mmol) 71%.

1.8 Benzylsulfonyl-D-Ser(Bz)-Gly-4-amidinobenzyl-amide×TFA 151 mg (0.433 mmol) of benzylsulfonyl-D-Ser(Bz)-OH and 121 mg (0.433 mmol) of H-Gly-4-amidinobenzylamide×2 HCl were dissolved in a little abs. DMF. While cooling with ice, 225 mg (0.433 mmol) of PyBOP and 230 μl (1.32 mmol) of DIEA were added. After it had been stirred at room temperature for 1 hr, the mixture was concentrated in vacuo and the product was purified by HPLC (acetonitrile/H₂O, 0.1% trifluoroacetic acid, elution at 37.4% acetonitrile).

Yield: 232 mg (0.356 mmol) 82%.

1.9 Benzylsulfonyl-D-Ser-Gly-4-amidinobenzylamide×HCl 50 mg of HPLC-purified benzylsulfonyl-D-Ser(Bz)-Gly-4-acetyloxamidinobenzylamide×TFA are dissolved in 50 ml of 90% acetic acid and hydrogenated, at room temperature for 48 hrs, using 50 mg of 10% palladium on active charcoal. After that, the catalyst is filtered off and the filtrate is concentrated in vacuo. The product is purified by HPLC (acetonitrile/H₂O containing 0.1% TFA, elution on analytical HPLC at 21.4% acetonitrile) and converted into the HCl form using an ion exchanger.

Yield: 20 mg (0.041 mmol) 54%.

1.10 Benzylsulfonyl-D-Ser(COO-isobutyl)-Gly-4-amidino-benzylamide×HCl 30 mg (0.062 mmol) of benzylsulfonyl-D-Ser-Gly-4-amidinobenzylamide×HCl are dissolved, at room temperature, in 3 ml of pyridine in the added presence of 1 ml of acetonitrile. 16.1 μl (0.124 mmol) of isobutyl chloroformate are added while cooling with ice. The mixture is stirred for 30 minutes while cooling with ice and then stirred overnight at room temperature. The solvent is removed in vacuo and the product is purified by HPLC (elution on analytical HPLC at 37.9% acetonitrile) and converted into the HCl form using an ion exchanger.

Yield: 13 mg (0.022 mmol)=36%.

IMPLEMENTATION EXAMPLE 2

Inhibiting urokinase with selected compounds in which Y=amidino

Determining the inhibitory effect:

In order to determine the inhibitory effect, 200 μl of Tris buffer (0.05 M, 0.154 M NaCl, 5% ethanol, pH 8.0; contains the inhibitor), 25 μl of substrate (Bz-βAla-Gly-Arg-pNA in H₂O) and 50 μl of sc-urokinase were incubated at 25° C. After 3 min, the reaction was interrupted by adding 25 μl of acetic acid (50%) and the absorption was determined at 405 nm using a microplate reader (Dynatech MR 5000). The $K_i$ values were determined in accordance with Dixon (Biochem. J. 55, 170–171, 1953) by linear regression using a computer program. The $K_i$ values are the mean of at least three determinations.

Abbreviations employed:

| | |
|---|---|
| Ac | acetyl |
| Boc | tert-butyloxycarbonyl |
| Bz | benzyl |
| DIEA | diisopropylethylamine |
| DMF | N,N-dimethylformamide |
| PyBOP | benzotriazol-1-yl-N-oxytris(pyrrolidino)-phosphonium hexafluorophosphate |
| TEA | triethylamine |
| TFA | trifluoroacetic acid |
| THF | tetrahydrofuran |
| CMe | cyclohexylmethyl |
| iBu | iso-butyl |

What is claimed is:

1. A urokinase inhibitor of the formula I:

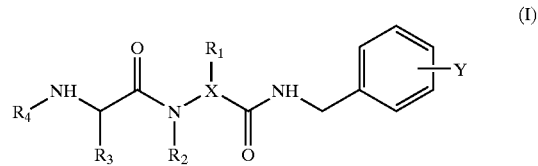

(I)

in which the substituent Y can be present in the 3 position or 4 position and is an amidino group

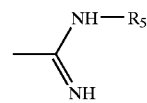

in which $R_5$ is an H, an OH or a carbonyl radical —CO—R or oxycarbonyl radical —COO—R, where R can be a branched or unbranched alkyl having 1–16 C atoms, a substituted or unsubstituted aryl or heteroaryl radical or a substituted or unsubstituted aralkyl or heteroaralkyl radical,
  X is a CH group or N,
  R1 is H or a branched or unbranched alkyl having 1–8 C atoms or a $(CH_2)_n$—OH in which n=1–5,
  $R_2$ is an H or a branched or unbranched alkyl having 1–8 C atoms,

| $R_4$ | Configuration of $R_3$ | $R_3$ | $R_2$ | X—$R_1$ | Position of amidino | $K_i$, μM |
|---|---|---|---|---|---|---|
| H | L | CH₂—OH | H | CH₂ | 4 | 21 |
| Boc | L | CH₂—OH | H | CH₂ | 4 | 23 |
| H | D | CH₂—OH | H | CH₂ | 4 | 12 |
| Ac | D | CH₂—OH | H | CH₂ | 4 | 41 |
| Bz—SO₂ | D | CH₂—OH | H | CH₂ | 4 | 0.036 |
| CMe—SO₂ | D | CH₂—OH | H | CH₂ | 4 | 0.048 |
| Bz—SO₂ | D | CH₂—O—Bz | H | CH₂ | 4 | 0.84 |
| Bz—SO₂ | D | CH₂—OH | H | CH₂—CH₃ | 4 | 0.0077 |
| Bz—SO₂ | D | CH₂—O—COO—CH₃ | H | CH₂ | 4 | 0.39 |
| Bz—SO₂ | D | CH₂—O—COO-iBu | H | CH₂ | 4 | 0.50 |
| Bz—SO₂ | D | CH₂—O—COO-iBu | H | CH₂—CH₃ | 4 | 0.043 |
| H | D | CH₂—O—Bz | H | CH₂ | 3 | >1 000 |
| Boc | D | CH₂—O—Bz | H | CH₂ | 3 | >1 000 |
| Bz—SO₂ | D | CH₂—O—Bz | H | CH₂ | 3 | >1 000 |

R₃ is a $(CH_2)_n$—OH in which n=1–5 or is a branched or unbranched alkyl having 1–8 C atoms or is present in prodrug form and is a $(CH_2)_n$—OX in which n=1–5, where X can be an alkyl, aralkyl or aralkylcarbonyl radical or a corresponding oxycarbonyl radical, and R₄ is a sulfonyl radical —$SO_2$—R, a carbonyl radical —CO—R, an oxycarbonyl radical —COO—R or an H, where R is a branched or unbranched alkyl having 1–16 C atoms, a substituted or unsubstituted aryl or heteroaryl radical, a substituted or unsubstituted aralkyl or heteroaralkyl radical or an adamantyl radical or a camphor radical.

2. A urokinase inhibitor as claimed in claim 1, characterized in that the amidino group in the amidinobenzylamide is in the 4 position and in that the amino acids Gly and D-Ser, and also an arylsulfonyl radical or an aralkylsulfonyl radical, as R₄, are bonded to it.

3. A method of controlling tumors comprising administering to a patient a urokinase inhibitor as claimed in claim 1.

4. The method as claimed in claim 3, characterized in that the urokinase inhibitor is in the form of a tablet, sugar-coated tablet, capsule, pellet, suppository, solution or plaster, etc.

5. The method as claimed in claim 3, characterized in that the urokinase inhibitor is administered orally, subcutaneously, intravenously, or transdermally.

* * * * *

UNITED STATES PATENT AND TRADEMARK OFFICE
CERTIFICATE OF CORRECTION

PATENT NO. : 6,831,196 B2
DATED : December 14, 2004
INVENTOR(S) : Stürzebecher et al.

It is certified that error appears in the above-identified patent and that said Letters Patent is hereby corrected as shown below:

Title page,
Item [75], Inventors, add -- Sebastian Künzel, Jena (DE) --.

Column 5,
Lines 51 and 54, replace "$CH_2$-$CH_3$" with -- $CH$-$CH_3$ --.
Line 65, replace "$\mu I$" with -- $\mu l$ --.

Column 6,
Line 64, replace "R1" with -- $R_1$ --.

Signed and Sealed this

Twenty-fourth Day of May, 2005

JON W. DUDAS
*Director of the United States Patent and Trademark Office*